(12) United States Patent
Sar et al.

(10) Patent No.: US 10,495,492 B2
(45) Date of Patent: Dec. 3, 2019

(54) MULTIPLE AXIS SELF-CONTAINED SPHERICAL SENSOR SYSTEM

(71) Applicant: Raytheon Company, Waltham, MA (US)

(72) Inventors: David R. Sar, El Segundo, CA (US); David D. Crouch, Eastvale, CA (US); Michael J. Holihan, Santa Clarita, CA (US); Devon G. Crowe, Tucson, AZ (US)

(73) Assignee: RAYTHEON COMPANY, Waltham, MA (US)

( * ) Notice: Subject to any disclaimer, the term of this patent is extended or adjusted under 35 U.S.C. 154(b) by 178 days.

(21) Appl. No.: 15/874,329

(22) Filed: Jan. 18, 2018

(65) Prior Publication Data

US 2019/0219425 A1 Jul. 18, 2019

(51) Int. Cl.
*G01D 11/24* (2006.01)
*G01D 11/26* (2006.01)

(52) U.S. Cl.
CPC .......... *G01D 11/245* (2013.01); *G01D 11/26* (2013.01)

(58) Field of Classification Search
CPC .............................. G01D 11/245; G01D 11/26
USPC ....................................................... 250/239
See application file for complete search history.

(56) References Cited

U.S. PATENT DOCUMENTS

| | | | | |
|---|---|---|---|---|
| 4,821,043 A | * | 4/1989 | Leavitt | H01Q 1/28 343/765 |
| 6,129,307 A | * | 10/2000 | Deoms | F41G 3/22 244/3.16 |
| 6,145,393 A | * | 11/2000 | Canton | G01C 21/18 248/550 |
| 6,484,978 B2 | * | 11/2002 | Voigt | G01C 21/18 248/182.1 |
| 6,952,151 B2 | | 10/2005 | French | |
| 7,905,463 B2 | | 3/2011 | Burnham | |
| 8,074,394 B2 | | 12/2011 | Lowrey, III | |
| RE45,824 E | | 12/2015 | French | |

* cited by examiner

*Primary Examiner* — Seung C Sohn
(74) *Attorney, Agent, or Firm* — Cantor Colburn LLP

(57) ABSTRACT

A multi-axis self-contained sensor system includes an outer spherical housing and an inner spherical housing. The outer spherical housing has a transparent spherical shell that surrounds a first cavity and having a first refractive index (RI). The inner spherical housing is in the first cavity and is completely surrounded by the outer spherical housing. The inner spherical housing has a first average density and includes a spherical wall that surrounds a second cavity. A sensor system is contained in the second cavity, and a suspending fluid layer is interposed between the outer spherical housing and the inner spherical housing. The suspending fluid layer is composed of a fluid having a second RI.

20 Claims, 9 Drawing Sheets

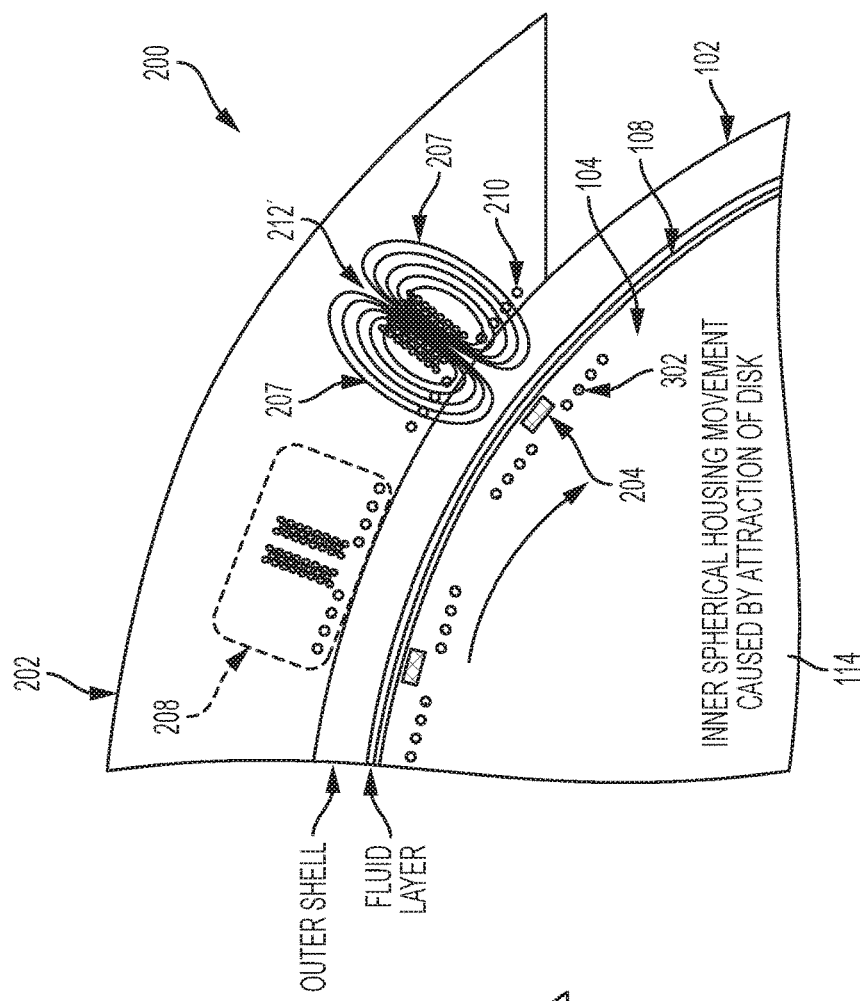
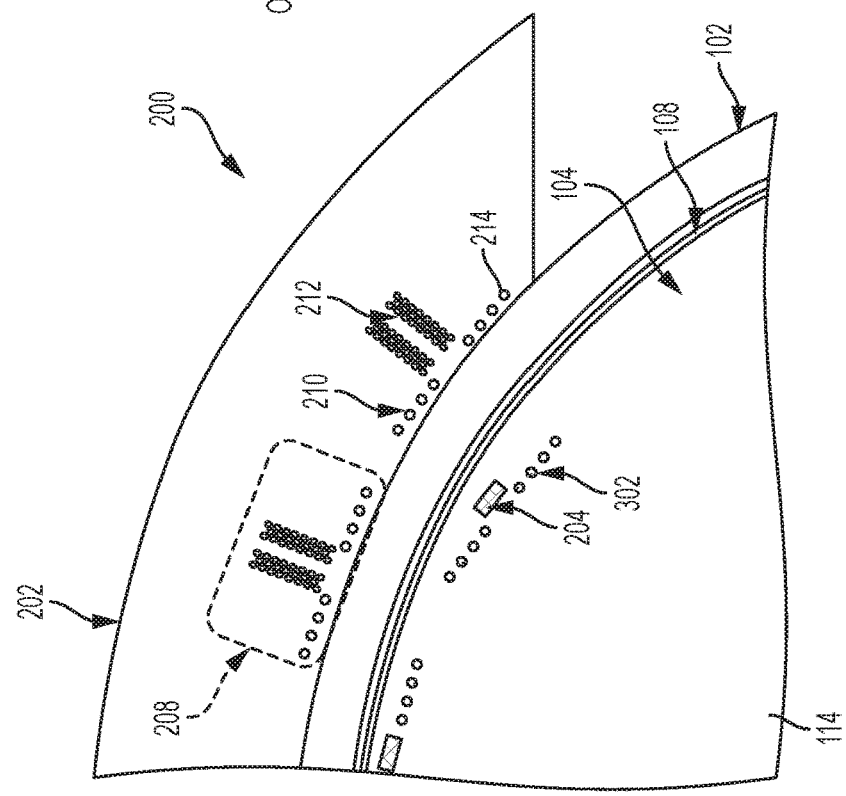

MULTIPLE AXIS SELF-CONTAINED SPHERICAL SENSOR SYSTEM

BACKGROUND

The subject matter disclosed herein relates to electrical sensors, and more particularly, to multi-axis sensor assemblies.

The development of unmanned vehicles (UVs) and drones, both air, ground, and maritime, has increased demands for sensor systems that can be installed on UV/drone platforms, and more traditional platforms, to provide operators with a wide variety of data types relevant to the specific mission at hand. These directional sensor systems (including, but not limited to, optical, RF, electromagnetic, acoustical, atomic force, magnetic, etc.) aim to maximize the relevant data that can be relayed to the operator. Traditional optical systems, as one of several possible examples, include one or more imaging cameras that are installed on a miniaturized single-axis or dual-axis rotatable gimbal. The gimbal and camera are then collectively hard mounted to the UV or drone. However, the FOV achieved by these single-axis or dual-axis gimbal assemblies is still limited. Therefore, the operator is typically required to also adjust the position of the platform itself, e.g., tilting and/or rotating the platform, to further aim the camera. The limitations described in the above example also hold for other sensor types such as radars, spectrometers, Hall Effect probes, etc.

BRIEF DESCRIPTION

According to a non-limiting embodiment, a multi-axis self-contained sensor system includes an outer spherical housing and an inner spherical housing. The outer spherical housing has a transparent spherical shell that surrounds a first cavity and having a first refractive index (RI). The inner spherical housing is in the first cavity and is completely surrounded by the outer spherical housing. The inner spherical housing has a first average density and includes a spherical wall that surrounds a second cavity. A sensor system is contained in the second cavity, and a suspending fluid layer is interposed between the outer spherical housing and the inner spherical housing. The suspending fluid layer is composed of a fluid having a second RI.

According to another non-limiting embodiment, a method of energizing a multi-axis self-contained sensor system comprises disposing an inner spherical housing completely within an outer spherical housing that contains a suspension fluid. The inner spherical housing is configured to float in the suspension fluid so as to move according to three degrees of freedom with respect to the outer spherical housing. The method further includes coupling a plurality of receiving inductors and a plurality of steering receptors to the inner spherical housing. The method further includes wirelessly transmitting a control signal from an external source located remotely from the outer spherical housing to the plurality of receiving inductors and the plurality of steering receptors such that the plurality of receiving inductors and the plurality of steering receptors are energized.

BRIEF DESCRIPTION OF THE DRAWINGS

The following descriptions should not be considered limiting in any way. With reference to the accompanying drawings, like elements are numbered alike:

FIGS. 7A-7B are block diagrams illustrating operation of the motion control system included with the multi-axis self-contained sensor system according to a non-limiting embodiment;

DETAILED DESCRIPTION

A detailed description of one or more embodiments of the disclosed system, apparatus and method are presented herein by way of exemplification and not limitation with reference to the Figures.

Various non-limiting embodiments described herein provide a balanced, low friction, nested spherical platform for pointing and controlling directional sensors (optical, RF, electromagnetic, acoustical, atomic force, magnetic, Etc.) in a manner that does not constrain them to fixed or predetermined axes. Additional non-limiting embodiments also provide a sensor platform capable of supplying wireless command, communication, and control (C3) signals, and/or wirelessly supplying electric power, to the aforementioned spherical platform and sensors, allowing completely unconstrained motion.

At least one non-limiting embodiment provides a multiple axis (multi-axis) self-contained spherical sensor system, where the enact sensor or combination of sensors can vary widely, depending on the specific needs of the user. Examples of sensors includes, but are not limited to, optical, RF, electromagnetic, acoustical, atomic force, magnetic, etc., which have a directional nature that requires pointing or aiming for optimal functionality.

The sensor system includes an inner spherical housing nested (i.e., contained) within an outer spherical housing. The inner spherical housing includes various electronic sensor components that establish an electronic sensor system which may include one or more of the sensors described previously. The outer spherical housing is composed of a high-strength rigid transparent material capable of protecting the nested sphere from damage and which may be transparent and capable of taking an optical grade polished surface, depending on the sensors' requirements. A suspending fluid layer is interposed between the inner spherical housing and the outer spherical housing. The suspending fluid is composed of a transparent (to light, RF, magnetic field, Etc. depending on the sensor) material, chosen for minimal viscosity, which allows the nested inner spherical housing to move along three degrees of freedom (3DOV) with respect to the outer protective sphere. In at least one embodiment, the nested inner spherical housing has the same density as the suspending fluid, thereby placing the imaging system in neutral buoyancy. In this manner, the inner spherical housing containing the imaging system is free to "float" within the outer spherical housing without limitation from mechanical components or linkages found in traditional gimbal assemblies. While the following example uses an optical camera and rangefinder as representative sensors, this may also be applied to other types of sensors.

Figure 1:
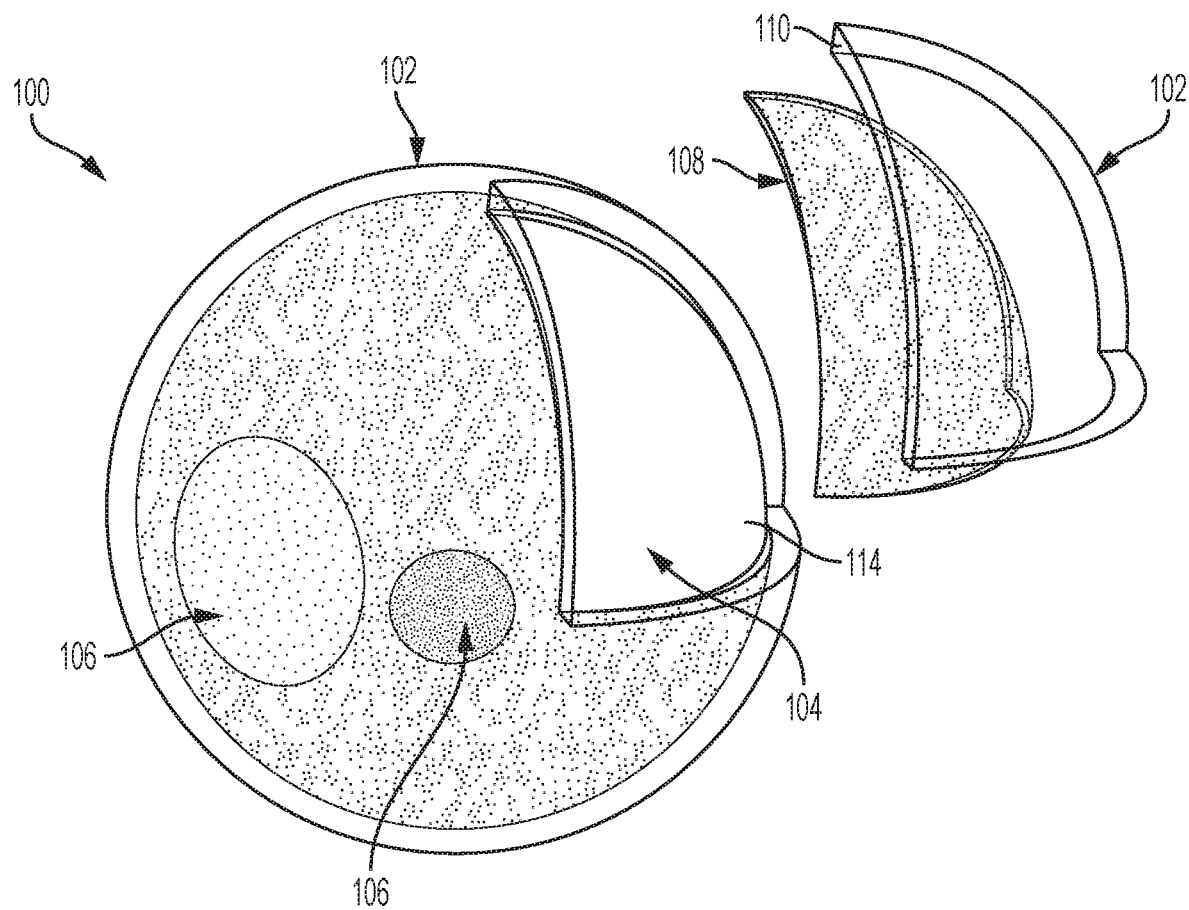
FIG. 1 is a partial cutaway view of a multi-axis self-contained sensor system according to a non-limiting embodiment.

With reference now to FIG. 1, a multi-axis self-contained sensor system 100 is illustrated according to a non-limiting embodiment. The multi-axis self-contained sensor system 100 includes an outer spherical housing 102, and an inner spherical housing 104 including an electronic sensor (imaging system, in this example) 106. The multi-axis self-contained sensor system 100 further includes a suspending fluid layer 108 interposed between the outer spherical housing 102 and the inner spherical housing 104, and allows the inner spherical housing 104 to freely rotate about three axes, i.e., three degrees of freedom (3DOF).

Figure 3:
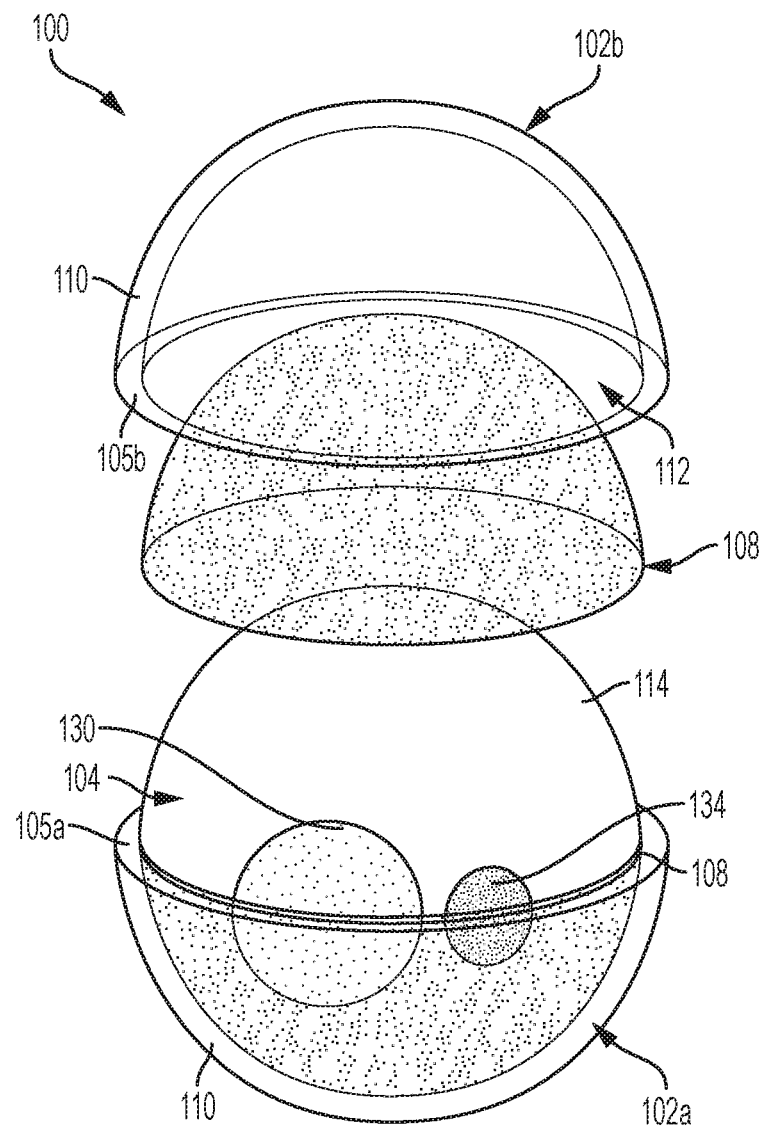
FIG. 3 is a disassembled view of the multi-axis self-contained sensor system according to a non-limiting embodiment.

The outer spherical housing 102 has a transparent spherical shell 110 that surrounds a first cavity 112 (see FIG. 3). The transparent spherical shell 110 is composed of a rigid material including, but not limited to, glass, plastic, ceramic, and sapphire. The transparent spherical wall 110 has a thickness ranging, for example, from about 5 millimeters (mm) to about 30 mm depending upon specific applications, and a first refractive index (RI) ranging, for example, from 1.33 to 3.0 depending upon the application and region of interest in the optical spectrum.

The inner spherical housing 104 is disposed in the first cavity 112 and is completely surrounded by the outer spherical housing, 102. The inner spherical housing 104 has a spherical wall 114 that completely surrounds a second cavity 116 (see FIG. 2). The spherical wall 114 is composed of a rigid material including, but not limited to, glass, plastic, acrylic and ceramic. The spherical wall 114 has a first average density ranging, for example, from about 1.5 grams per cubic centimeter to 7.0 grams per cubic centimeter depending upon specific applications, and a thickness ranging, for example, from about 0.3 cm to about 1.5 cm.

Figure 2:
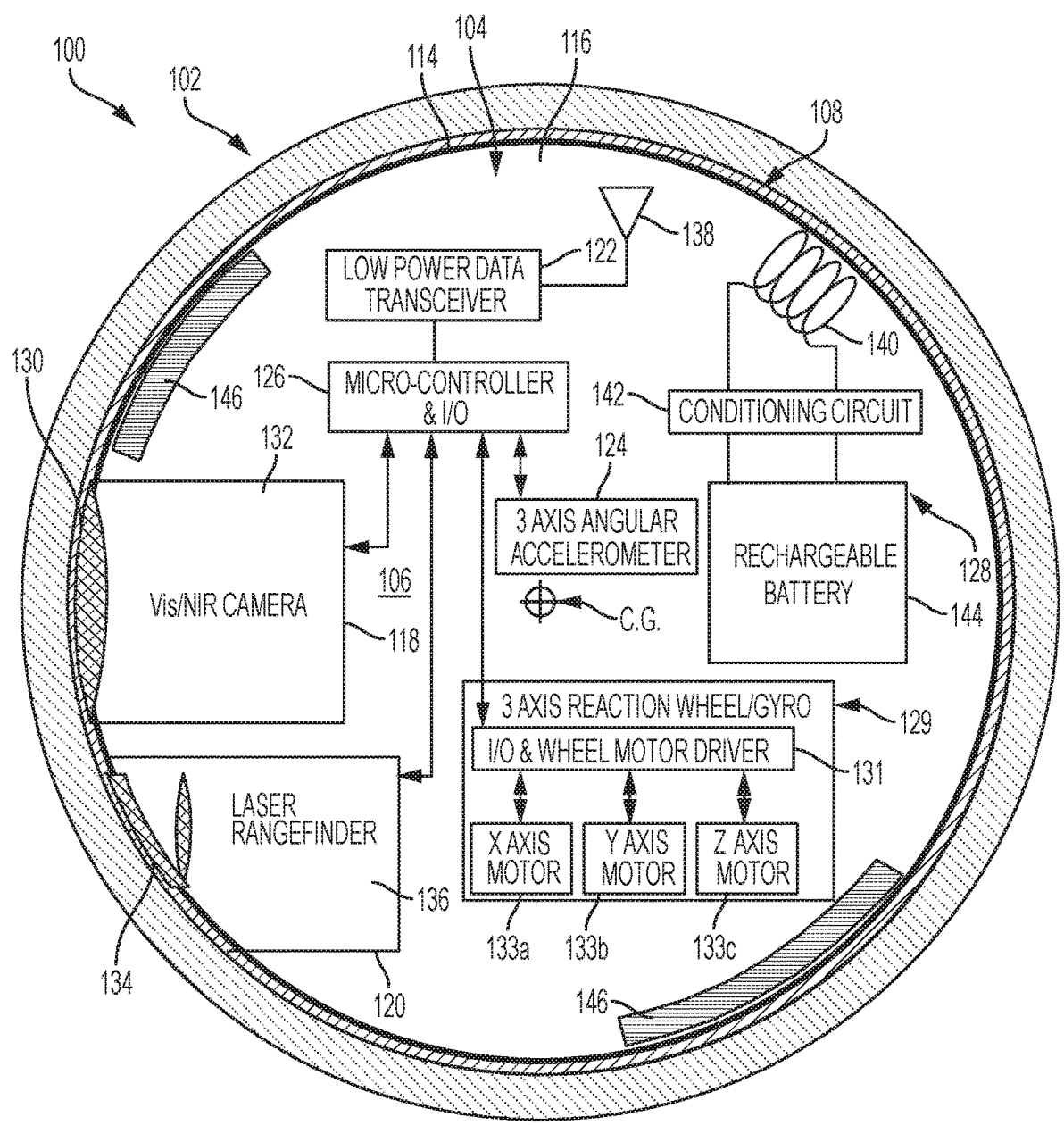
FIG. 2 is a block diagram of an imaging system contained within an inner spherical housing of the multi-axis self-contained sensor system according to a non-limiting embodiment.

The sensor (imaging system in this example) 106 is contained in the inner cavity 116 of the inner spherical housing 104. An example of an imaging system 106 that can be implemented in the multi-axis self-contained sensor system 100 is illustrated in FIG. 2. The example imaging system 106 includes a camera system 118, a rangefinder system 120, a transceiver 122, an accelerometer 124, a microcontroller 126, and a battery system 128. Although an imaging system is described, the multi-axis self-contained sensor system 100 could be employed with other types of sensors such as, for example, radio frequency (RF) sensors, electromagnetic sensors, acoustical sensors, atomic force sensors, magnetic sensors, etc.

The example camera system 118 includes a camera lens 130 in optical/electrical communication with a camera controller 132. The camera system 118 is configured to capture an image viewed through the lens 130. The camera system 118 includes, for example, a near infrared (NIR) camera or a visible spectrophotometry (VIS) camera.

The rangefinder system 120 includes an objective lens 134 in signal communication with a rangefinder controller 136. The objective lens includes, for example, an aberration corrector which allows the rangefinder system 120 to measure a distance between a target object and/or target area viewed through the objective lens 134 and the multi-axis self-contained sensor system 100.

The transceiver 122 is configured to receive a power signal and/or a data signal via one or more antennas 138. In at least one embodiment, the transceiver 122 can receive a high frequency data signal and/or high frequency control signal from an exterior transmitter, and can deliver the data signal and control signal to the micro-controller 126. Likewise, the transceiver 122 can take digital signals from the microcontroller 126 and transmit them to an exterior receiver. In at least one embodiment, the transceiver 122 can also exchange data using optical signal transmission.

The angular accelerometer 124 is configured to measure the proper angular acceleration, i.e., the acceleration (or rate of change of angular velocity) of the inner spherical housing 104. An acceleration signal is then output to the microcontroller 126, which is indicative of the measured proper angular acceleration and rate.

The micro-controller 126 is in signal communication with the sensor systems 118, and 120 (which in this example is a camera and rangefinder), the transceiver 122, and the accelerometer 124. The microcontroller 118 can include an electronic microprocessor having electronic memory that stores computer readable instructions that, when executed by the microprocessor, execute various operations of the imaging system 106 and/or generate various controls signals that operate the different components (e.g., camera system 118, rangefinder system 120, etc.) of the imaging system 106.

The battery system 128 includes a battery charging inductor 140, a power-conditioning circuit 142, and a rechargeable battery 144. The battery charging inductor 140 receives wirelessly transmitted energy. The received energy induces alternating current (AC) flow through the battery charging inductor 140, which is transferred to the power conditioning circuit 142. The power conditioning circuit 142 converts the AC into direct current (DC), which charges the rechargeable battery 144. In at least one non-limiting embodiment, the power condition circuit 142 is constructed as a rectifier circuit.

The inner spherical housing 104 further includes one or more balancing elements 146. The balancing elements 146 may be formed on an inner surface of the spherical wall 114, and can be formed of a rigid material including, but not limited to metal and/or polymer. The balancing elements 146 have a mass that, in at least one embodiment, may be configured to balance the inner spherical housing 104 with its center of gravity (C.G.) located at the geometric center of the sphere within the suspending fluid layer 108. The balancing elements 146 can also be used to fine tune the average density of the inner spherical housing 104 to match that of the suspending fluid layer 108.

FIG. 2 also illustrates the multi-axis self-contained sensor system 100 including a triple-axis gyro/momentum wheel unit 129. The triple-axis gyro/momentum wheel unit 129 includes an I/O-wheel motor driver circuit 131, an X-axis motor 133a, a Y-axis motor 133b and a Z-axis motor 133c. The I/O-wheel motor driver circuit 131 includes an input in signal communication with the micro-controller 124, and one or more outputs in signal communication with the motors 133a, 133b and 133c. Each motor 133a, 133b and 133c is coupled to a rotational momentum wheel (not shown in FIG. 2).

The momentum wheels are capable of rotating in a direction that is orthogonal to one another. For example, a first wheel coupled to the X-axis motor 133a can rotate forward and backwards along the X-axis direction. A second wheel coupled to the Y-axis motor 133b can rotate forward and backwards along the Y-axis direction. A third wheel coupled to the Z-axis motor 133c can rotate forward and backwards along the Z-axis direction. The triple-axis gyro/momentum wheel unit 129 receives power and/or position control signals from the micro-controller 124. Based on the position control signals, the I/O-wheel motor driver circuit 131 drives one or more of the motors 133a, 133b and/or 133c, which in turn rotates a respective wheel. Through the physics principal of conservation of angular momentum, rotation of one or more of the wheels induces motion of the inner spherical housing 104 as described in greater detail below The suspending fluid layer 108 is interposed between the outer spherical housing 102 and the inner spherical housing 104. In at least one embodiment, the transparent spherical shell 110 and the spherical wall 114 directly contact the suspending fluid layer 108. The suspending fluid layer 108 is composed of a transparent fluid selected to meet several criteria including, but not limited to, properties such as density, refractive index, viscosity (as low as possible), freezing/boiling point, and compatibility with respect to the other materials of the inner and outer spheres. Examples of candidate fluids may include, but are not limited to, water based solutions such as propylene/ethylene glycol solutions or brines, as well as various fluorinated hydrocarbon fluids and light mineral or silicone oils. The fluid used for the suspending fluid layer 108 can be selected to have an average second density that is equal to, or approximately equal to, the average density of the inner spherical housing 104. In this manner, the inner spherical housing 104 can be neutrally buoyant within the suspending fluid 108. The fluid type and/or the fluid thickness can also set a selected refractive index (RI) of the suspending fluid layer 108. In at least one embodiment, the suspending fluid 108 has a RI that is equal to, or approximately equal to, the RI of the outer spherical housing.

A method of assembling a multi-axis self-contained sensor system 100 is described with reference to FIGS. 3 and 4. Initially, the outer spherical housing 102 can be formed as two separate and individual hemispheres, e.g. a lower hemisphere 102a and an upper hemisphere 102b, as illustrated in FIG. 3. Each hemisphere 102a and 102b includes a hollowed cavity for receiving the inner spherical housing 104. The inner spherical housing 104 is then disposed in one of the hemispheres, e.g., lower hemisphere 102a. The remaining hemisphere, e.g., the upper hemisphere 102b, can be brought into contact with the lower hemisphere 102a at the inner edges 105a and 105b to define a bonding interface. The lower hemisphere 102a and the upper hemisphere 102b can then be bonded together at the bonding interface using, for example, an adhesive film or adhesive silicone, or ultraviolet cure optical resin. In at least one embodiment, the adhesive has an RI that matches the RI of the outers spherical housing 102.

Figure 4:
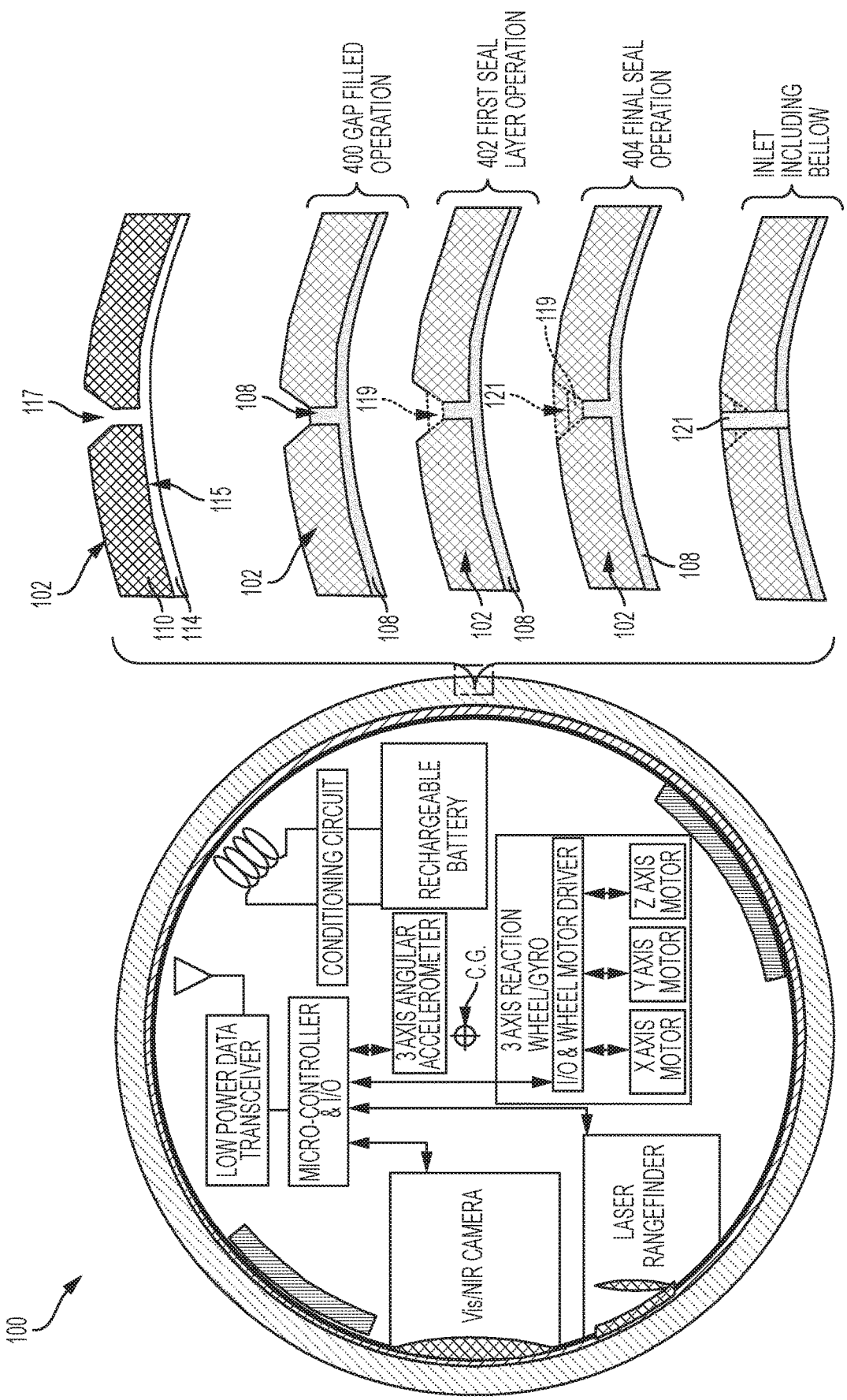
FIG. 4 is a series of diagrams illustrating a process flow of depositing a suspending fluid layer in the multi-axis self-contained sensor system according to a non-limiting embodiment.

Once the hemispheres 102a and 102b are bonded together to form the outer spherical housing 102, the inner spherical housing 104 is completely contained therein, while a gap 115 is formed between the transparent spherical shell 110 and the spherical wall directly 114 of the inner spherical housing 104 as shown in FIG. 4. An inlet 117 can also be formed in the transparent shell 110 or at the bonding interface which allows access to the gap 115. The suspending fluid 108 can then be injected through the inlet 117 to fill the gap 115 (see operation 400). Accordingly, the inner spherical housing 104 is placed into buoyance and is allowed to "float" in the suspending fluid 108. After depositing the suspending fluid 108, the inlet 117 can be filled with an adhesive or sealant material. In at least one embodiment, a dual-sealing process can be used. For example, a first sealing layer 119 can be deposited in the inlet 117 (see operation 402). The upper surface of the first sealing layer 119 and inlet can then be cleaned to remove irregularities, dust, dirt, etc., and a second sealing layer 121 can then be deposited on the first sealing layer 119 to completely fill the inlet 117 (see operation 404). In at least one embodiment, the sealed inlet 117 can include a bellows (not shown). The bellows can be disposed in the inlet to allow the suspending fluid 108 to expand or contract based on temperatures surrounding the outer spherical shell 102.

Figure 5:
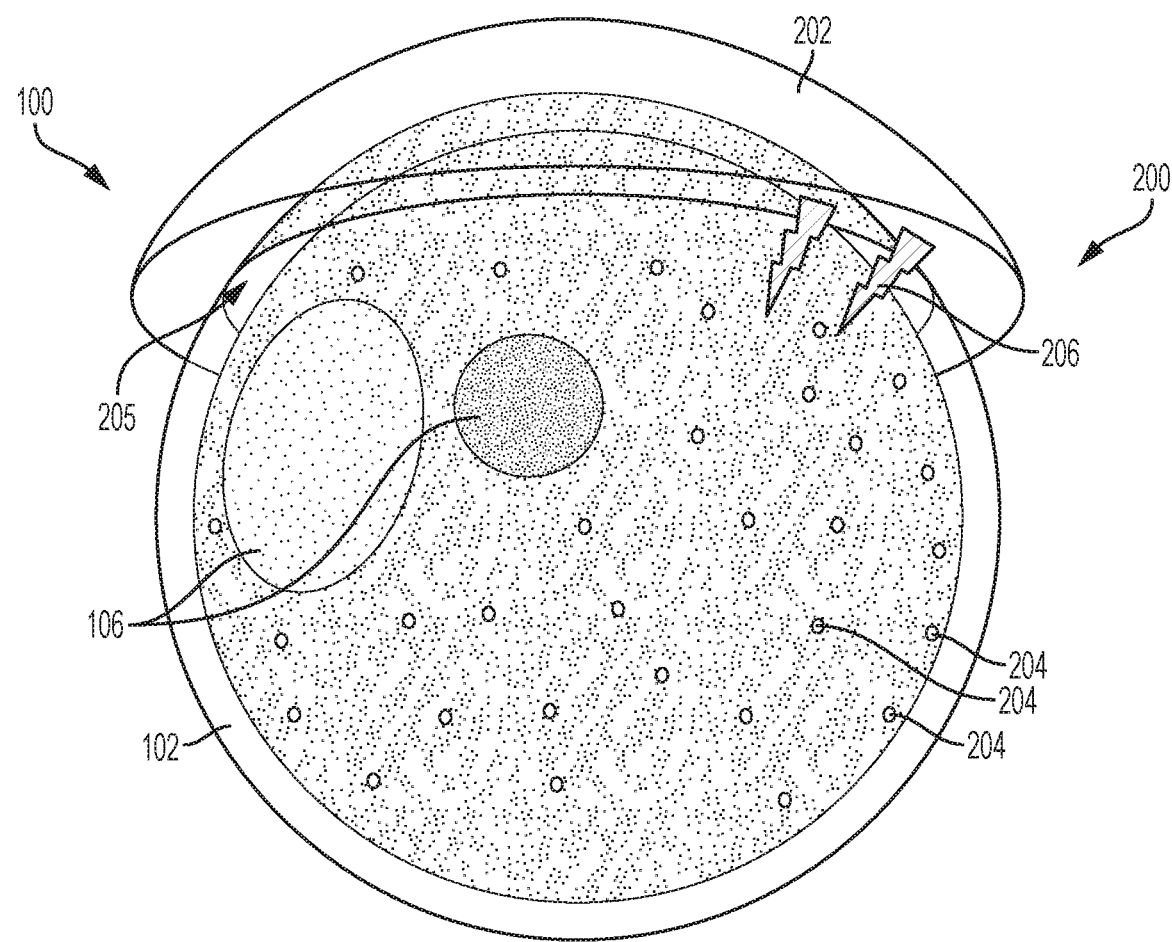
FIG. 5 illustrates a motion control system included with the multi-axis self-contained sensor system according to a non-limiting embodiment.

Turning to FIG. 5, the multi-axis self-contained sensor system 100 is illustrated implementing a motion control system 200. The motion control system 200 is in electrical communication with the inner spherical housing 104 (covered by the outer spherical housing 102 in FIG. 5), and is configured to move the inner spherical housing 104 along three degrees of freedom (3DOF) with respect to the outer spherical housing 102.

In at least one embodiment, the motion control system 200 includes a control base 202, and a plurality of steering receptors 204. The control base 202 is disposed adjacent the outer spherical housing 102. In at least one embodiment, the control base 202 has a concaved shape that defines a socket 205 configured to receive and support the outer spherical housing 102. In at least one embodiment, the outer spherical housing 102 is fixed with respect to control base 202, and the control base 202 outputs an electrical signal 206, which can be received by the imaging system 106 contained within the inner spherical housing 104. For example, the electrical signal 206 can include a high-frequency data signal received by the transceiver 122 (not shown in FIG. 5) and/or a low-frequency power signal received by the battery system 128 (not shown in FIG. 5).

Figure 6:
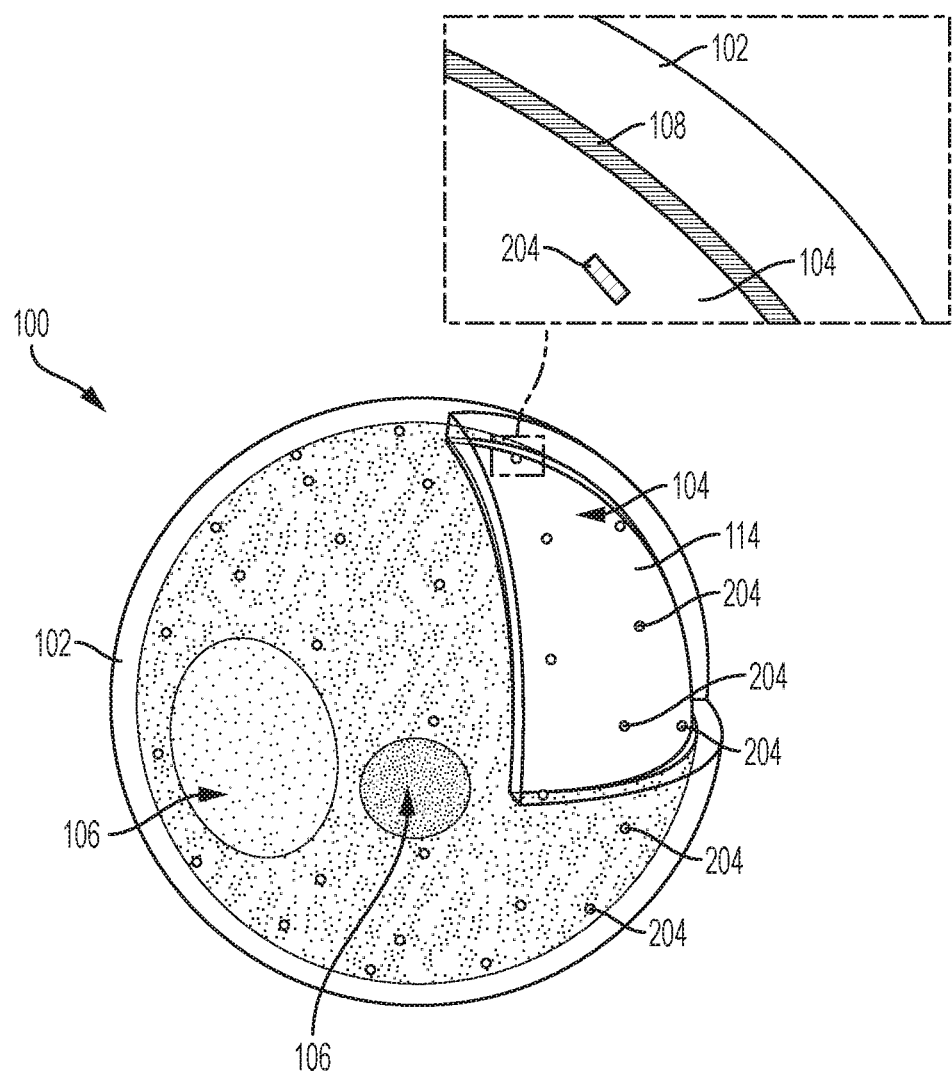
FIG. 6 is a partial cutaway view of the multi-axis self-contained sensor system including steering receptors coupled to the inner spherical housing of the multi-axis self-contained sensor system according to a non-limiting embodiment.

Turning to FIG. 6, the steering receptors 204 are formed integrally with the spherical wall 114 of the inner spherical housing 104. For example, the steering receptors 204 can be formed on or beneath the surface of the spherical wall 114. Each steering receptor 204 can be composed of a ferromagnetic material. The ferromagnetic material can include, cobalt (Co), samarium (Sm), or any ferromagnetic material that is magnetically attracted to an electromagnetic field. In at least one embodiment, the steering receptors 204 may be magnetized. The steering receptors 204 can be utilized to facilitate rotation of the inner spherical housing 104 along three-degrees of freedom as described in greater detail below.

Turning to FIGS. 7A and 7B, the control base 202 is illustrated in greater detail. The control base 202 includes a plurality of signal transmitters 208 configured to generate the electrical signal. Each signal transmitter 208 includes a base inductor 210 and a solenoid 212. The base inductor 210 is configured to induce electrical current in receiving inductor 302 when they happen to overlap each other so as to generate the electrical power to charge the internal battery within 104. The electrical signal can include an electromagnetic field 207 that is generated from an energized solenoid 212' in response to external steering command signals.

In at least one embodiment, the base inductor 210 includes a plurality of flat spiral coils 214 that forms an electrical conductor. The flat spiral coils 214 are formed integrally with the control base 202. For example, the coils 214 of the inductors 210 can be embedded in the control base 202 and/or formed as electrically conductive traces on the control base 202 using an additive manufacturing process such, for example, as three-dimensional (3D) printing or inkjet printing. Voltage can be applied to the coils 214, which in turn induces electrical current flow through the coils 214. Accordingly, the control base 202 can receive a voltage from an external power supply (not shown), and deliver the voltage to one or more base inductors 210. The base inductor 210 becomes electrically stimulated, and in turn generates the electrical current which energizes a corresponding solenoid 302 in inner spherical wall 114, supplying power to recharge the battery internal to 104. Inductor 210 may also be used to transmit high frequency data magnetically to the transceiver antenna internal to inner sphere 104 (138 in FIG. 2).

As described above, a plurality of steering receptors 204 are coupled to the inner spherical housing 104, and are composed of a ferromagnetic material that is magnetically attracted to an electromagnetic field (e.g., electromagnetic field 207). The steering receptors 204 can be used in conjunction with the control base 202 to facilitate 3DOF rotational movement of the inner spherical housing 104 with respect to the outer spherical housing 102. For example, the inner spherical housing 104 is illustrated in a first position at FIG. 7A. While in this first position, the steering receptor 204 is illustrated as being offset or vertically unaligned with respect to an un-energized solenoid 212. Turning to FIG. 7B, however, the solenoid 212' is energized so as to induce an electromagnetic field 207, which in turn applies a magnetic force on to the steering receptor 204. As a result, the steering receptor 204 is forced (i.e., magnetically pulled) toward the energized solenoid 212'. Because the steering receptor 204 is coupled to the inner wall 114, the inner spherical housing 104 is forced to rotate toward the energized solenoid 212' (as indicated by the arrow), with the suspending fluid layer 108 serving as a 3DOF bearing that allows the inner spherical housing 104 to rotate with respect to the outer spherical housing 102. Varying the number of energized solenoids' 212 and/or the level of electrical current supplied to the base inductor 210 can adjust (i.e., increase/decrease) the magnetic force applied to a steering receptor 204, thereby allowing for fine tuning of the inner spherical housing's position.

Figure 8:
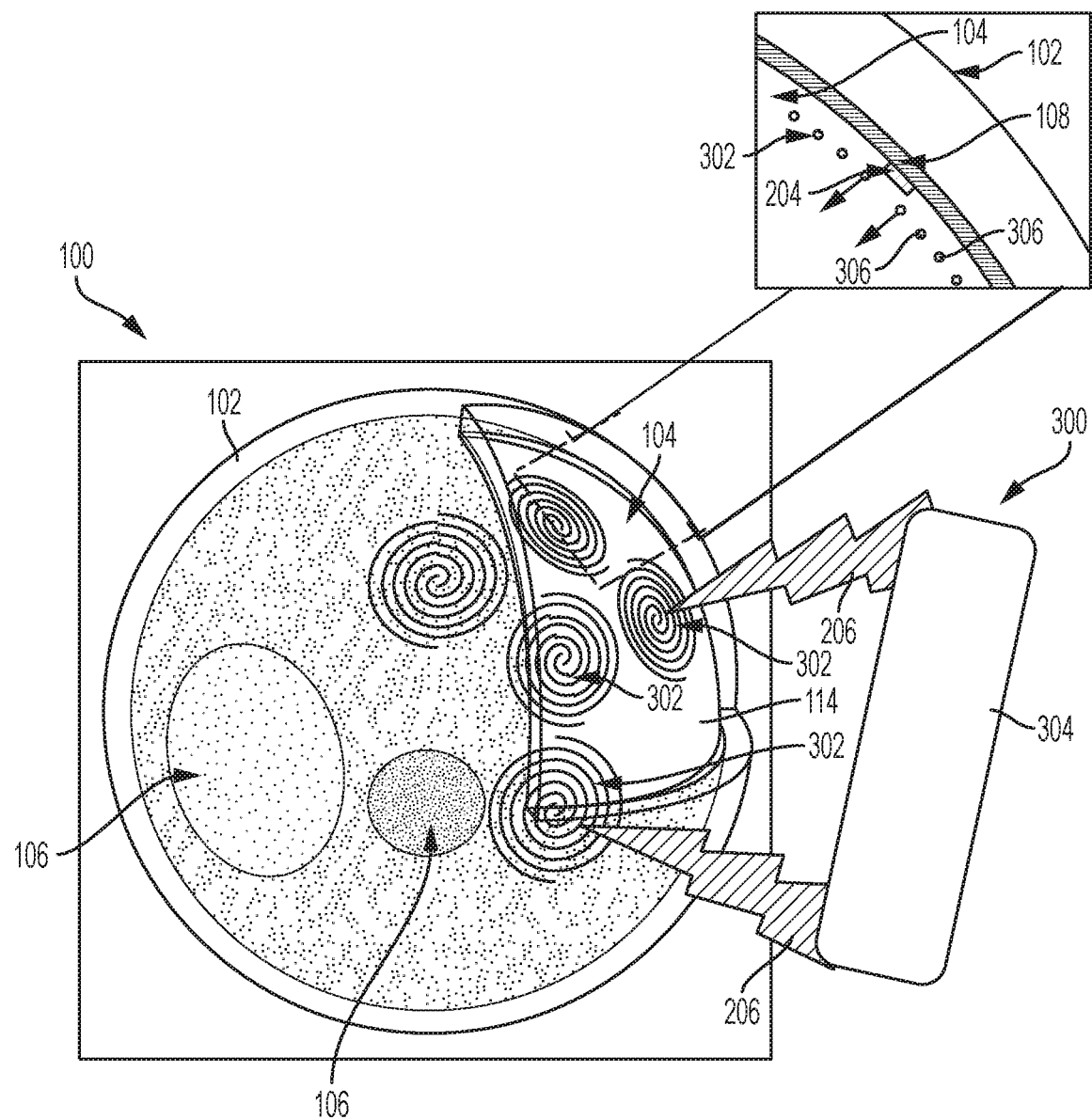
FIG. 8 illustrates a wireless energy transmission system included with the multi-axis self-contained sensor system according to a non-limiting embodiment.

Turning now to FIG. 8, the multi-axis self-contained sensor system 100 is illustrated implementing a wireless energy transmission system 300. The wireless energy transmission system 300 is configured to wirelessly receive an electrical signal 206, and deliver the signal 206 to the imaging system 106 contained within the second cavity (not shown in FIG. 8) of the inner spherical housing 104. The wireless energy transmission system 300 includes a plurality of receiving inductors 302 that can electrically communicate with a power/data source 304. In at least one embodiment, the power/data source 304 can communicate (i.e., provide power and/or exchange data) with inductor 302 via inductor 210 (shown in FIGS. 7A and 7B). The power/data source 304 can include the control base 202 described above or any other source that provides a power signal and/or data signal 206 to the receiving inductors 302.

The receiving inductors 302 are coupled with the spherical wall 114 of the inner spherical housing 104. In at least one embodiment, each receiving inductor 302 includes a plurality of flat spiral coils 306 that form a flat spiral-shaped electrical conductor. The flat spiral coils 306 can be embedded in the spherical wall 114 and/or formed as an electrically conductive trace on a surface of the spherical wall 114 using an additive manufacturing process such as three-dimensional (3D) printing or inkjet printing. Each receiving inductor 302 can operate as a near-field antenna that receives the power signal and/or the data signal 206, and in turn communicates the signal 206 to the imaging unit 106 contained within the inner cavity of the inner spherical housing 104. For example, each receiving inductor 302 can electrically communicate with the transceiver 122 and/or the battery system 128. In this manner, one or more of the receiving inductors 302 can deliver a power signal to the transceiver 122 and/or the battery system 128. The power signal can power the micro-controller 126 (and the other imaging components) and/or charge the rechargeable battery 144. Similarly, one or more of the receiving inductors 302 can deliver the data signal to the transceiver 122, which in turn can be relayed to the image processor 126 for further processing, and/or relayed to other components included in imaging system 106.

Figure 9:
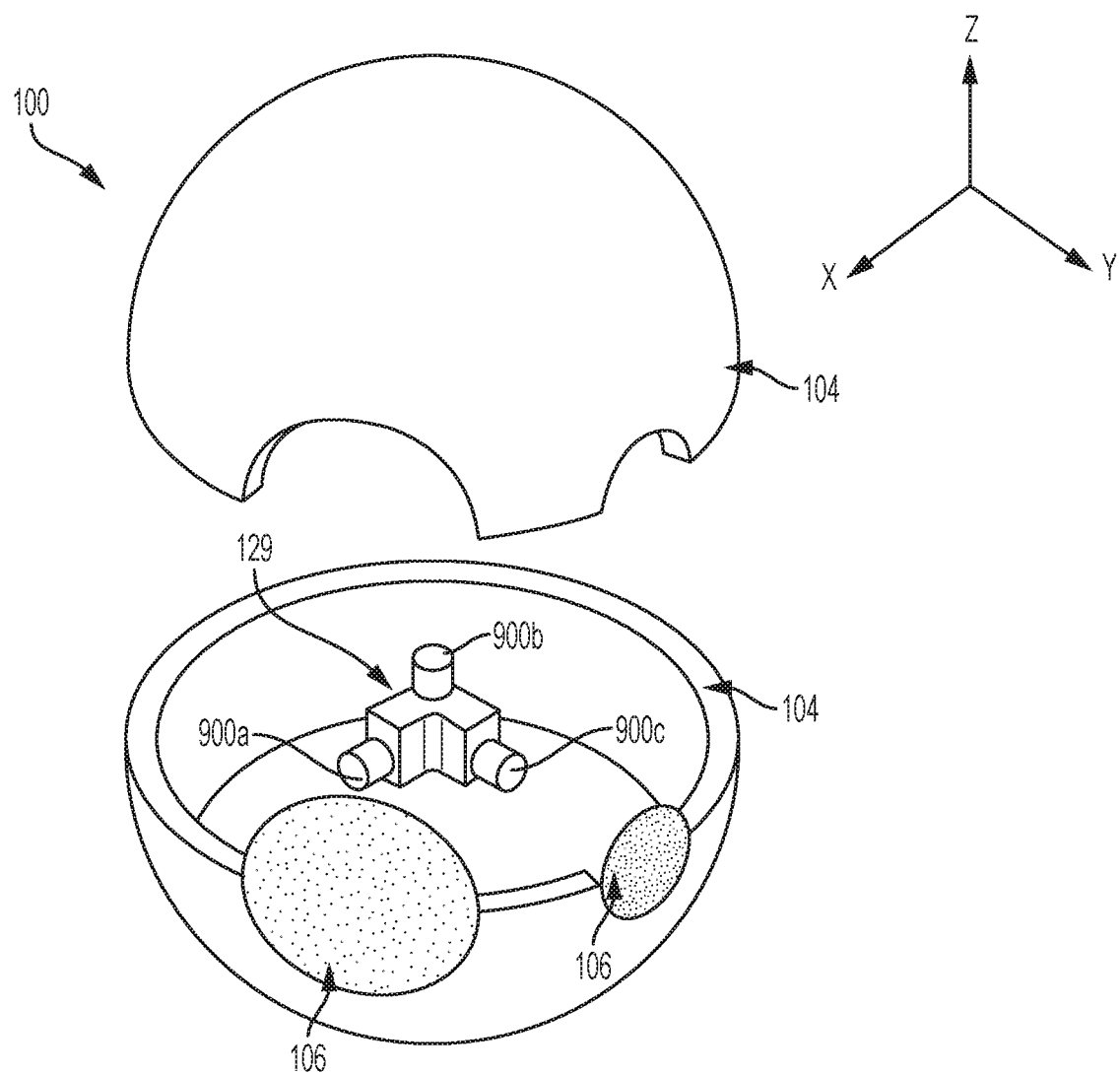
FIG. 9 illustrates a wireless energy transmission system including a triple-axis gyro/momentum wheel unit implemented in the inner spherical housing according to a non-limiting embodiment.

Turning now to FIG. 9, the triple-axis gyro/momentum wheel unit 129 is shown implemented in the inner spherical housing 104 according to a non-limiting embodiment. In addition to the electromagnetic solenoid induced movement of the inner spherical housing 104 described above, the triple-axis gyro/momentum wheel unit 129 can provide gyroscopic stabilization of inner sphere housing 104, along with providing an alternate or supplemental means to induce motion of the inner sphere housing 104 independent of the solenoids 212 and steering receptors 204 previously described herein (see e.g., FIGS. 7A-7B).

In at least one embodiment, command signals, either external, and/or as a result of feedback from the accelerometers and microprocessor, cause one or more of the three orthogonal momentum wheels 900a, 900b and/or 900c to begin rotating via electric motors included in the gyro/momentum wheel unit 129 (see FIG. 2). Through the physics principal of conservation of angular momentum, rotation of one or more of the wheels 900a, 900b and/or 900c induces motion of the inner spherical housing 104, which is opposite to the rotational direction of the wheels 900a, 900b and/or 900c. Due to the low friction environment of the inner spherical housing 104 floating within the suspending fluid 108 (not shown in FIG. 9), the induced motion results in considerable rotation of the inner spherical housing 104. Using more than one of the three orthogonal wheels 900a, 900b and/or 900c, along with varying their rotational rates, can allow for any rotational vector to be chosen. The wheels can also be rotated in a direction opposite to the direction at which the inner spherical housing 104 is traveling in order to stabilize the inner spherical housing 104.

It is envisioned that the multi-axis self-contained sensor system 100 described herein may be applied to other technical fields including, but not limited to, optical prosthetics. For example, the outer spherical housing 102 can be formed with a size of a human eyeball, and an image camera sensor can installed within the inner spherical housing 104 contained in the outer spherical housing 102. The outer spherical housing can be composed of a biocompatible material such as glass, or acrylic, for example, while the suspension fluid 108 can be composed of a non-toxic solution such as, for example, saline. Examination of the cross-section of a human eye socket serving to support the outer spherical housing 102 has shown enough area and volume to fit energy and control electronics for moving the inner spherical housing 104 as described herein.

As described above, various non-limiting embodiments provide a multi-axis self-contained spherical sensor system which overcomes the mechanical constraints (e.g., mechanical bearings, hubs, wire harnesses, etc.) of a traditional gimbal assembly by nesting an inner sphere within a transparent outer protective sphere. A suspension fluid layer is located between the inner sphere and the protective sphere, which allows the inner sphere to move along 3DOF to provide a maximum FOV. The self-contained spherical sensor system also improves durability by nesting the inner sphere containing various electronic imaging components within a durable outer protective sphere. Accordingly, the inner sphere containing the various electrical components of the sensor system is protected from damage caused by blunt force, weather, etc.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A multi-axis self-contained sensor system comprising:
   an outer spherical housing having a transparent spherical shell that surrounds a first cavity and having a first refractive index (RI);
   an inner spherical housing in the first cavity and completely surrounded by the outer spherical housing, the inner spherical housing having a first average density and including a spherical wall that surrounds a second cavity; and
   a sensor system contained in the second cavity; and
   a suspending fluid layer interposed between the outer spherical housing and the inner spherical housing, the suspending fluid layer composed of a fluid having a second RI.

2. The multi-axis self-contained sensor system of claim 1, wherein the suspending fluid has a second average density that is about equal to the first average density of the inner spherical housing such that the inner spherical housing is neutrally buoyant within the suspending fluid.

3. The multi-axis self-contained sensor system of claim 1, further comprising a motion control system in electrical communication with the inner spherical housing, and configured to rotationally translate the inner spherical housing along three degrees of freedom with respect to the outer spherical housing.

4. The multi-axis self-contained sensor system of claim 3, wherein the motion control system further comprises:
   a control base disposed adjacent the outer spherical housing and configured to output an electrical signal; and
   a plurality of steering receptors coupled to the inner spherical housing and configured to move in response to the electrical signal so as to rotationally translate the inner spherical housing with respect to the outer spherical housing.

5. The multi-axis self-contained sensor system of claim 4, wherein the control base further comprises:
   a plurality of signal transmitters configured to generate the electrical signal, each signal transmitter comprising:
      a solenoid to generate a magnetic field that induces inner spherical housing rotational motion; and
      a base inductor configured to produce magnetic fields for inductive power transfer to the inner spherical housing.

6. The multi-axis self-contained sensor system of claim 5, wherein the base inductor includes a flat spiral electrical conductor, the flat spiral conductor formed integrally with the control base, wherein the electrical signal is an electromagnetic field that is generated from an energized solenoid in response to flowing the electrical current through the base inductor.

7. The multi-axis self-contained sensor system of claim 6, wherein each steering receptor is composed of a ferromagnetic material configured to be magnetically attracted to the electromagnetic field generated by an energized solenoid.

8. The multi-axis self-contained sensor system of claim 4, wherein the steering receptors are formed integrally with the spherical wall of the inner spherical housing.

9. The multi-axis self-contained sensor system of claim 1, further comprising a wireless energy transmission system configured to wirelessly receive and deliver power and data to the second cavity.

10. The multi-axis self-contained sensor system of claim 9, wherein the wireless energy transmission system comprises a plurality of receiving inductors formed integrally with the spherical wall of the inner spherical housing, each receiving inductor in signal communication with the sensor system.

11. The multi-axis self-contained sensor system of claim 10, wherein each receiving inductor is configured to receive and deliver power and data to the components contained in the second cavity.

12. The multi-axis self-contained sensor system of claim 11, wherein the sensor system comprises:
   at least one sensor configured to output a signal indicative of a measured result;
   a transceiver configured to receive at least one of a power signal and a data signal;
   a sensor controller in signal communication with the transceiver and the sensor system, and configured to exchange data with the sensor system; and
   a battery system including a power conditioning circuit in signal communication with a rechargeable battery.

13. The multi-axis self-contained sensor system of claim 12, wherein each receiving inductor is in signal communication with the transceiver to deliver the data signal, and with the power conditioning circuit to deliver the power signal to charge the rechargeable battery.

14. The multi-axis self-contained sensor system of claim 3, wherein the motion control system further comprises a triple-axis gyro/momentum wheel unit comprising three orthogonal momentum wheels configured to rotate, wherein rotation of at least one of the momentum wheels induces rotational motion of the inner spherical housing 104 with respect to the outer spherical housing.

15. A method of energizing a multi-axis self-contained sensor system, the method comprising:

disposing an inner spherical housing completely within an outer spherical housing that contains a suspension fluid, the inner spherical housing configured to float in the suspension fluid so as to rotate according to three degrees of freedom with respect to the outer spherical housing;

coupling a plurality of receiving inductors and a plurality of steering receptors to the inner spherical housing; and wirelessly transmitting a control signal from an external source located remotely from the outer spherical housing to the plurality of receiving inductors and the plurality of steering receptors such that the plurality of receiving inductors and the plurality of steering receptors are energized.

16. The method of claim 15, wherein wirelessly transmitting the control signal includes transferring at least one of a power and a data signal from the plurality of receiving inductors to an image system contained within the inner spherical housing.

17. The method of claim 15, wherein wirelessly transmitting the control signal to energize the at least one of the plurality of steering receptors to thereby adjust a position of the inner spherical housing with respect to the outer spherical housing.

18. The method of claim 17, wherein the plurality of steering receptors are composed of a ferromagnetic material, and transmitting the control signal includes generating an electromagnetic field so as to magnetically attract at least one of the steering receptors toward the electromagnetic field transmitting thereby moving the inner spherical housing with respect to the outer spherical housing.

19. The method of claim 18, wherein transmitting the control signal includes:

positioning a control base adjacent to the outer spherical housing such that outer spherical housing rotates with respect to the control base;

embedding at least one solenoid and at least one base inductor in the control base; and energizing the base inductor so as to flow electrical current around the solenoid to generate the control signal.

20. The method of claim 19, further comprising varying the level of electrical current supplied to the base inductor to adjust a magnetic force applied to a steering receptor and tune a position the inner spherical housing with respect to the outer spherical housing.

* * * * *